(12) United States Patent
Feiweier et al.

(10) Patent No.: US 8,180,128 B2
(45) Date of Patent: May 15, 2012

(54) METHOD FOR RECORDING MEASURED DATA OF A PATIENT WHILE TAKING ACCOUNT OF MOVEMENT OPERATIONS, AND AN ASSOCIATED MEDICAL DEVICE

(75) Inventors: Thorsten Feiweier, Poxdorf (DE); Ralf Ladebeck, Erlangen (DE); Diana Martin, Herzogenaurach (DE); Hartwig Newiger, Nürnberg (DE); Josef Pfeuffer, Newton, MA (US); Michael Szimtenings, Bonn (DE); Harald Werthner, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 958 days.

(21) Appl. No.: 12/219,613

(22) Filed: Jul. 24, 2008

(65) Prior Publication Data

US 2009/0041318 A1 Feb. 12, 2009

(30) Foreign Application Priority Data

Jul. 26, 2007 (DE) .......................... 10 2007 034 953

(51) Int. Cl.
*G01R 33/56* (2006.01)
*G01R 33/54* (2006.01)

(52) U.S. Cl. ...................................................... 382/128

(58) Field of Classification Search .................. 382/128, 382/131
See application file for complete search history.

(56) References Cited

U.S. PATENT DOCUMENTS

| | | | | |
|---|---|---|---|---|
| 5,999,588 A | * | 12/1999 | Shao et al. ........................ | 378/4 |
| 7,248,725 B2 | * | 7/2007 | Zwirn et al. ................... | 382/128 |
| 7,378,660 B2 | * | 5/2008 | Case et al. ............... | 250/363.01 |
| 7,697,738 B2 | * | 4/2010 | Da Silva et al. .............. | 382/128 |
| 7,756,307 B2 | * | 7/2010 | Thielemans ................... | 382/128 |
| 7,787,675 B2 | * | 8/2010 | Pan et al. ...................... | 382/128 |

(Continued)

FOREIGN PATENT DOCUMENTS

DE 102 31 061 1/2004

OTHER PUBLICATIONS

German Office Action issued Feb. 14, 2008.

*Primary Examiner* — W. B. Perkey
(74) *Attorney, Agent, or Firm* — Harness, Dickey & Pierce, P.L.C.

(57) ABSTRACT

A method is disclosed for recording measured data of a patient while taking account of movement operations by way of a medical device that is designed both for recording movement-related measured data, in particular measured data of high temporal resolution and/or measured data that can be interpolated with regard to movement operations, with the aid of an imaging method and/or by means of at least one sensor element, and also for recording nuclear medicine measured data, in particular of lower temporal resolution. In at least one embodiment, the method includes recording nuclear medicine measured data with the aid of the medical device; simultaneously recording movement-related measured data with the aid of the medical device; determining at least one item of movement information relating to at least one movement operation of the patient and/or in the body of the patient by evaluating at least a portion of the recorded measured data of high temporal resolution on the part of a computing device of the medical device; and adapting at least one item of attenuation correction information available for the computing device and serving for reconstructing the nuclear medicine measured data, doing so as a function of the at least one determined item of movement information.

18 Claims, 1 Drawing Sheet

U.S. PATENT DOCUMENTS

| | | | |
|---|---|---|---|
| 2005/0226527 A1* | 10/2005 | Weese et al. | 382/275 |
| 2006/0237652 A1* | 10/2006 | Kimchy et al. | 250/363.02 |
| 2007/0131858 A1* | 6/2007 | Wollenweber et al. | 250/252.1 |
| 2008/0095414 A1* | 4/2008 | Desh et al. | 382/128 |
| 2008/0107229 A1* | 5/2008 | Thomas et al. | 378/4 |
| 2008/0135769 A1* | 6/2008 | Rosen | 250/363.09 |
| 2009/0037130 A1* | 2/2009 | Feiweier et al. | 702/104 |
| 2009/0076379 A1* | 3/2009 | Hamill et al. | 600/424 |
| 2010/0239134 A1* | 9/2010 | Koehler et al. | 382/128 |

* cited by examiner

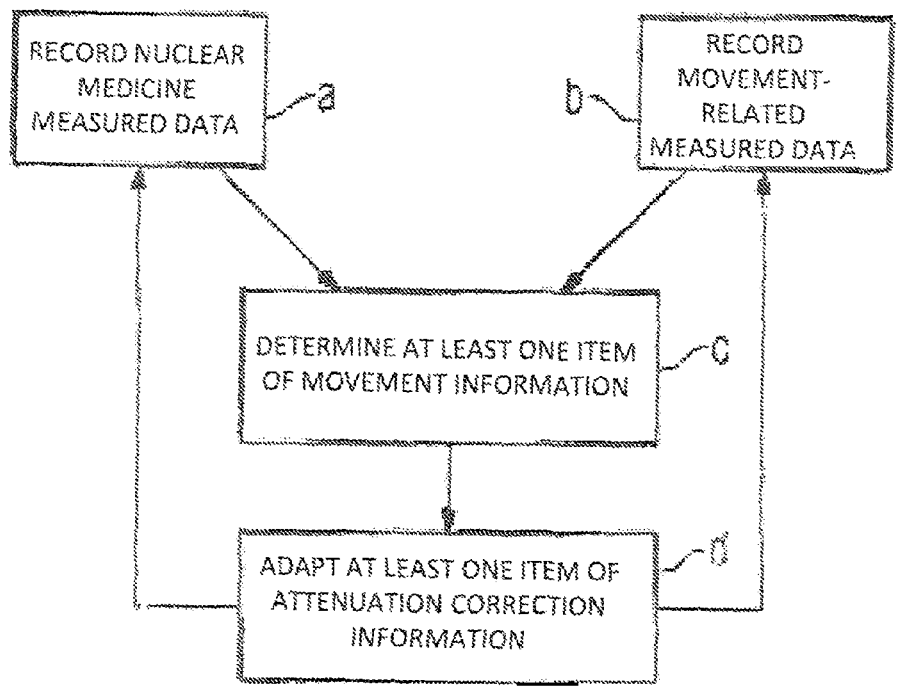
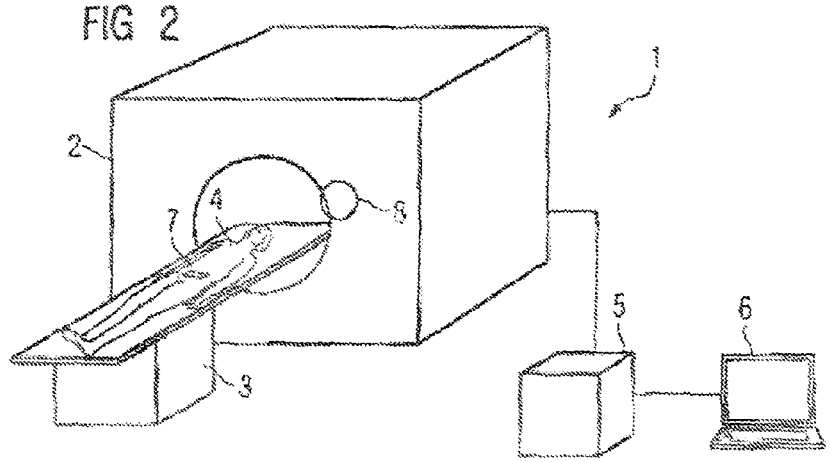
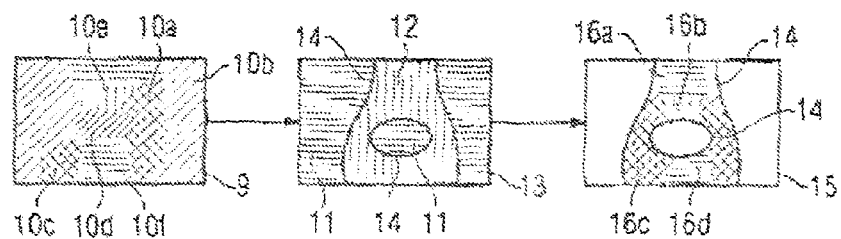

METHOD FOR RECORDING MEASURED DATA OF A PATIENT WHILE TAKING ACCOUNT OF MOVEMENT OPERATIONS, AND AN ASSOCIATED MEDICAL DEVICE

PRIORITY STATEMENT

The present application hereby claims priority under 35 U.S.C. §119 on German patent application number DE 10 2007 034 953.1 filed Jul. 26, 2007, the entire contents of which is hereby incorporated herein by reference.

FIELD

Embodiments of the invention generally relate to a method for recording measured data of a patient while taking account of movement operations by way of a medical device that is designed both for recording movement-related measured data, in particular measured data of high temporal resolution and/or measured data that can be interpolated with regard to movement operations, with the aid of an imaging method and/or by way of at least one sensor element, and also for recording nuclear medicine measured data, in particular of lower temporal resolution and a corresponding imaging medical device.

BACKGROUND

In the case of image reconstruction are used on various occasions so-called attenuation corrections are in nuclear medicine imaging, for example in positron emission tomography (PET). In the case of PET imaging, light quanta emitted from annihilation of a positron and an electron in opposite directions are registered in the ideal case by a detector pair. This is done by measuring two events within a defined coincidence interval. In this case, the probability that these two light quanta follow their path without disturbance and largely rectilinearly depends, inter alia, on the absorption behavior of the material located in the path. Strongly absorbing materials such as, for example, bones, plastic and metals lead to a reduction in the detection rate.

This means, in turn, that without correction mechanisms the emission regions that lie "behind" absorbing regions are displayed in the image with an excessively low intensity (that is to say false quantification) or even in a distorted fashion (if there is an asymmetric absorption geometry). This is countered by the so-called attenuation correction (AC).

In the course of the attenuation correction, a spatial distribution of the absorption behavior is determined on the basis of models or a preceding measurement. In the simplest case, such a model can be spherical, such as, for example, in the case of head pictures. The measurements can be carried out with the aid of different modalities or of the nuclear medicine detectors themselves, for example with the aid of a PET detector and an additional rotating x-ray source. What is decisive is that the measurement can be used to say how the spatial distribution of the absorbing materials appears in the examination region.

In the case of combination of modalities (particularly hybrid modalities), with the aid of which both the taking of magnetic resonance tomography pictures and taking of nuclear medicine pictures are possible, the attenuation correction or an associated attenuation correction map is produced by and large with the aid of magnetic resonance tomography data.

However, there is a problem with the attenuation correction required for image reconstruction that the patient and, if appropriate, further constituents in the image region that are assigned to the patient or are arranged on the body of the latter or in the body of the patient can change their position during movement operations of the patient. During such movement operations, for example, periodic movement operations such as breathing or movement of the heart or else movements of limbs and the like, the attenuation correction map originally made no longer reproduces the current attenuation, as a result of which errors can occur when reconstructing the nuclear medicine images in the previously customary way with the aid of the initial attenuation correction map.

SUMMARY

In at least one embodiment of the invention a method is specified that is improved in this regard.

In at least one embodiment, there is provided a method for recording measured data of a patient while taking account of movement operations by means of a medical device that is designed both for recording movement-related measured data, in particular measured data of high temporal resolution and/or measured data that can be interpolated with regard to movement operations, with the aid of an imaging method and/or by way of at least one sensor element, and also for recording nuclear medicine measured data, in particular of lower temporal resolution, method including:
  recording nuclear medicine measured data with the aid of the medical device,
  simultaneously recording movement-related measured data with the aid of the medical device,
  determining at least one item of movement information relating to at least one movement operation of the patient and/or in the body of the patient by evaluating at least a portion of the recorded movement-related measured data on the part of a computing device of the medical device, and
  adapting at least one item of attenuation correction information available for the computing device and serving for reconstructing the nuclear medicine measured data, doing so as a function of the at least one determined item of movement information.

The starting point is therefore a medical device, in particular an imaging medical device, with the aid of which it is possible firstly to record the nuclear medicine measured data, in particular PET measured data, and secondly to record movement-related measured data of, for example, higher temporal resolution than is possible within the scope of the nuclear medicine method. The movement-related measured data can also alternatively or complementarily be interpolated for the purpose of determining movement between two movement detections. In this case, the temporally highly resolved data need not necessarily be image data, but can also, for example, be determined with the aid of one or more sensors (for example optically). The information of these sensors need not necessarily be capable of being displayed as an image.

For example, an imaging medical device can be a hybrid device that for the purpose of recording nuclear medicine measured data is also designed so as, for example, to record magnetic resonance data or computed tomography data. Supplementarily or alternatively, measured data can be recorded with the aid of one or more sensor elements in place of the possibility of recording magnetic resonance data, computed tomography data or ultrasound data and the like with an inventive medical device. For example, an optical or electrically operating sensor can be used in order to detect movement operations of high temporal resolution, or using interpolation methods.

During the nuclear medicine measurement, that is to say the PET measurement, for example, there is simultaneous recording, that is to say, if appropriate, recording conducted continuously or at fixed or varying intervals, of the movement-related measured data, for example of the higher temporal resolution by comparison with the nuclear medicine data recording. These movement-related measured data, for example in the form of measured data of a higher temporal resolution, are image data or other data, and serve (if appropriate, inter alia) the purpose of acquiring the movement of the examination object or of system components of the imaging device that move with the patient or because of the mobility of the patient. These measured data therefore have the purpose (if appropriate, in a fashion supplementing the obtaining of other information relating thereto) of obtaining at least one item of movement information that is in some way related to the movement of the patient or to the movement of patient-related device parts, and thus, for example, relates to the breathing of the patient or his cardiac movement, or to the movement of the body or of objects located on the body or in the vicinity, such as, for example, a mobile local coil or the like.

Finally, the movement information that has been obtained from the movement-related measured data of high temporal resolution, or by interpolation between movement detections, serves the purpose of adapting or correcting an item of attenuation correction information or a number of items of attenuation correction information, for example in the form of an attenuation correction map, in order to obtain a reconstruction of the nuclear medicine data starting from a "correct" (current) attenuation correction map.

The result according to at least one embodiment of the invention is that the attenuation correction information on which the reconstruction of the nuclear medicine data is based is corrected for movement such that the attenuation correction information is adapted to the current state of movement of the patient or of parts of the medical device that are connected to or associated with the movement of the patient.

The attenuation correction information to be adapted is stored in the computing device., for example as initial information from an attenuation correction measurement performed at the start of the data recording.

A substantially improved nuclear medicine imaging can thereby be achieved, since the exactitude of the attenuation correction information has a direct influence on the nuclear medicine image quality and the quantifiability.

According to at least one embodiment of the invention, at least one item of attenuation correction information forming a constituent of an attenuation correction map for a measured data recording range is adapted with particular advantage. In this case, a correction of the attenuation correction coefficients for the reconstruction of the nuclear medicine data by the movement correction rules from the measured data recording method, for example of a high temporal resolution, or with the aid of which the interpolatable data were obtained, is used in order to suitably adapt an attenuation correction map for a corresponding examination region or recording region in the body of a patient, or for a recording region of the (imaging) medical device. Thus, there is corrected for movement an attenuation correction map that reproduces for the recording region overall the spatial distribution of the absorption behavior of the tissue or of the other materials in the recording region.

At least one initial item of attenuation correction information, in particular an initial attenuation correction map, can be determined for later adaptation from already recorded movement-related measured data. Thus, in order for there to be present at the start of the measured data recording attenuation correction data that permit immediate or later reconstruction of the nuclear medicine measured data, an initial item of attenuation correction information, usually a plurality of such information items, is determined, preferably in the form of an initial attenuation correction map, to which end use is made of movement-related measured data already recorded previously, or of corresponding pictures, for example an attenuation correction map that was produced with the aid of magnetic resonance tomography data. This initial attenuation correction map, or the initial attenuation correction information items are then corrected later in the course of the inventive method, taking account of the determined movement information for the patient movement.

The at least one item of attenuation correction information can be adapted for a movement correction of the nuclear medicine measured data by using at least one imaging rule determined from the at least one item of movement information. It is thereby possible to make use of imaging rules that have, in any case, possibly been determined for a general movement correction.

The at least one or more items of attenuation correction information available to the computing device are advantageously classified as static or moving items of attenuation correction information, in which case in particular all items of attenuation correction information of an attenuation correction map are classified accordingly for a measured data recording range. The one item of attenuation correction information or the number of items of attenuation correction information are thus classified as static or moving, depending on whether they relate to static or movable measured data recording ranges. An attenuation correction map is correspondingly separated into static and movable components. If the attenuation correction information available to the computing device comes from an adaptation as a function of at least one item of movement information, this will relate to movable components if an adaptation in the sense of a movement-induced variation has taken place.

On the other hand, examples of static components to be named are ones that are to be ascribed to the absorption by a patient table (which usually does not move during a measurement) or cladding parts of the medical device. Movable components or items of attenuation correction information relate to the patient and, in the case of a corresponding, in particular imaging, medical device, to mobile (flexible) local coils that may be present and which have undefined positions, as well as patient fixings and the like.

At first, this classification is preferably performed initially, and is then adapted as a function of the movement information that is obtained during the inventive measured data recording. A single determination of fixed static (device-specific) components permits the adaptation of an attenuation correction map to be limited to specific regions.

In particular, this means that in the case where a classification into static and moving items of attenuation correction information has already been carried out at least once, a subsequent adaptation of at least one item of attenuation correction information can be carried out in such a way that exclusive account is taken of such items of attenuation correction information that have already been classified as moving. If appropriate, however, it is also possible to take account of specific regions that are neighboring in an attenuation map. It is thereby possible according to the invention to correct the movable components of an attenuation correction card with the aid of the simultaneously recorded movement information so as to achieve in this way an improvement in the nuclear medicine image quality, in particular in the event of strong movement. If only the attenuation correction information classified as moving correction information is taken into account, the outlay on calculation is simplified, since the static components do not require correction and so exclusive use of the moving attenuation correction information therefore does not give rise to any disadvantageous influencing of the image quality.

For example, at least one item of attenuation correction information relating to absorption by a patient table and/or at least one cladding part and/or a stationary local coil (for magnetic resonance recordings) of the medical device can be classified as static attenuation correction information, and/or at least one item of attenuation correction information relating to the patient and/or to a flexible local coil for a magnetic resonance data recording and/or to patient fixing can be classified as a moving item of attenuation correction information. The static attenuation correction information thus relates, for example, to the patient table that does not move during the measured data recording (if said table is moved during the data recording, there is a need for a classification as moving attenuation correction information) or parts of the cladding or other immobile parts of the imaging medical device. Such information that relates directly to movable device constituents and the patient can be classified as moving attenuation correction information and then be taken into account in the course of an adaptation, for example of the attenuation correction map. Examples to be mentioned are the patient himself or specific body parts of the patient, a flexible local coil that may be present for magnetic resonance pictures or patient fixings and the like.

At least one item of movement information relating to a relative movement of the patient in relation to a static component of the medical device can be determined from the recorded movement-related measured data (for example of high temporal resolution) and can be used to adapt the at least one item of attenuation correction information. Account is therefore taken of how the patient moves in relation to static components in the field of view of the modality (modalities). Such a definition of relative movements means that it is possible for the static position, for example of a patient couch or of another device constituent, such as of (fixed) local coils with a defined position to be suitably combined with the moving component or body part of the patient in an attenuation correction map.

Independently thereof, the stationary elements or device constituents for each type of (for example imaging) medical device such as, for example, a scanner and the like, can be defined once and then be stored in a computing device in the system.

According to at least one embodiment of the invention, magnetic resonance data and/or computed tomography data and/or ultrasound data and/or sensor data, in particular at least of an optical and/or electrical sensor element, can be recorded as movement-related measured data and/or positron emission tomography data and/or single photon emission computed tomography data can be recorded as temporally less well resolved nuclear medicine measured data. The movement-related, for example temporally highly resolved measured data can thus, for example, be data of a rapid imaging method such as magnetic resonance tomography or computed tomography or else ultrasound data. If appropriate, the movement information can also be determined from a combination of measured data obtained with different imaging methods, for example from fusion images from computed tomography and of an ultrasound method. Moreover, or alternatively, it is possible to use sensor elements that supply sensor data as measured data. In this case, the sensor data can be optical or electrical data and the like, from which movement information can be obtained, for example, camera data and the like.

Alongside the PET, the nuclear medicine method can be a further nuclear medicine method in the case of which use is made of attenuation correction information. If appropriate, it is also possible to use a number of nuclear medicine methods in combination with one another in the course of recording measured data with the aid of the (imaging) medical device.

According to at least one embodiment of the invention, in parallel with the measured data recording a movement correction can be performed in real time by the computing device for at least a portion of the nuclear medicine measured data as a function of the at least one determined item of movement information. The movement information is thus used not only for correcting the attenuation correction coefficients or for adapting them, but likewise for a movement correction of the nuclear medicine measured data, particularly in real time also leading to further continuous recording of measured data. This movement correction can be performed by taking account of imaging rules for the patient movement that have been obtained from the movement-related measured data for example of a temporally highly resolved method. Of course, the adaptation of the attenuation correction information can likewise be combined with a movement correction that is applied not in real time, but in retrospect, for example to the stored raw data of the nuclear medicine method. In each case, the movement information is then used not only for adapting an attenuation correction map and the like, but likewise for a (general) movement correction in order to improve the image quality of the nuclear medicine pictures.

Moreover, at least one embodiment of the invention relates to a medical device, for example an imaging medical device, that is designed for recording movement-related measured data of a patient while simultaneously taking account of movement operations, in particular measured data of a high temporal resolution and/or measured data that can be interpolated with regard to movement operations and for recording nuclear medicine measured data, in particular of a lower temporal resolution, and, in addition, to a computing device for determining at least one item of movement information relating to at least one movement operation of the patient and/or in the body of the patient, by evaluating at least a portion of the recorded movement-related measured data, and designed for adapting at least one item of attenuation correction information available to the computing device and serving for reconstructing the nuclear medicine measured data as a function of the at least one item of determined movement information. In this case, the (for example imaging) medical device is designed, in particular, for carrying out at least one embodiment of a method as outlined above.

The medical device therefore has a nuclear medicine recording device such as a positron emission tomograph. In addition, the device is also designed, for example, as hybrid modality for recording magnetic resonance data and/or computed tomography data or ultrasound data. As a supplement or alternative to imaging methods, it is possible to provide sensor elements such as optical or electrical sensors for recording measured data of a high temporal resolution. These sensor elements thus serve the purpose of obtaining movement information that is determined in supplementary or alternative fashion to magnetic resonance data and the like.

Moreover, the medical device has a computing device that derives from the highly resolved data at least one movement information item that is thereupon used to adapt an item of attenuation correction information to the current movement state of the system or of the patient. To this end, appropriate measured data processing algorithms are implemented on the computing device. In particular, the computing device can produce an adapted attenuation correction map that is based on the movement information that has currently been newly determined. The adaptation of the attenuation correction map therefore takes place in a fashion also leading to further data recording during measurement such that errors that may arise, in particular, in the case of strong movement are avoided in order to keep the image quality high.

BRIEF DESCRIPTION OF THE DRAWINGS

Further advantages, features and details of the invention emerge with the aid of the following drawings and from the example embodiments. In the drawings:

FIG. 1 shows a schematic sketch for carrying out an embodiment of the inventive method, FIG. 2 shows an inventive imaging medical device, and FIG. 3 shows a schematic sketch for an embodiment of the inventive adaptation of an attenuation correction map.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated. in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

A schematic sketch for carrying out an embodiment of the inventive method is illustrated in FIG. 1. Here, according to box a nuclear medicine measured data are recorded with the aid of an imaging medical device, while in accordance with box b the medical device likewise simultaneously records movement-related measured data, which are temporally highly resolved and can be interpolated with regard to movement operations, as image data or data of optical and/or electrical sensors, for example of a position sensor that detects the respiratory movement in one dimension. In this case, the nuclear medicine measured data are, for example, PET measured data, while the movement-related measured data can be data from magnetic resonance tomography, computed tomography, ultrasound data or data of optical or electrical and other sensor elements, it also being possible, if appropriate, to use a combination of different methods for recording the movement-related measured data which are, for example, temporally highly resolved.

Subsequently, for example, at specific time intervals while the measured data is still being recorded, in accordance with box c at least one item of movement information relating to at least one movement operation of the patient and/or in the body of the patient is determined by evaluating at least a portion of the recorded movement-related measured data with regard to their high temporal resolution or by interpolation on the part of a computing device of the imaging medical device. If the time resolution of the movement detection is not sufficiently high, it is possible to interpolate between two movement detections.

In accordance with box d, this one item, or this number of items, of movement information then serve the purpose of adapting at least one item of attenuation correction information, which is available to the computing device and serves for reconstructing the nuclear medicine measured data, as a function of the at least one determined item of movement information.

Thereafter, or in parallel therewith, the measured data can continue to be recorded, as is indicated by the arrows leading from box d to boxes a and b.

Thus, with the aid of an embodiment of the inventive method, the movement information determined in accordance with box c from the movement-related data is applied to the data of the attenuation correction in order to adapt at least the movable components of a corresponding attenuation correction map or in general an item of attenuation correction information that is subject to movement influences, and thus to correct the data, if appropriate as a function of the recorded movement operations of the patient, that is to say, for example, of the movement of the limbs, of the body or of movement operations in the body such as breathing and the like, or of device parts associated with the patient's movement.

During an adaptation on an attenuation correction map, the correction is expediently performed for the movable parts of the attenuation correction map, the static components identified as such remaining unchanged. This classification can be determined once with the aid of the movement information from the pictures, with the result that the static parts are no longer taken into account for the adaptation in future. Furthermore specific stationary or static elements can be defined from the start for the (imaging) medical device, for example a patient table that is always brought into an identical position for recording operation, cladding parts and the like.

FIG. 2 shows an inventive imaging medical device 1 that has a tomograph 2 in the case illustrated for recording magnetic resonance data and PET measured data. In other example embodiments, other image recording methods such as, for example, computed tomography or ultrasound methods, can be used. Likewise, other nuclear medicine recording methods can be provided. Furthermore, the movement operations can be tracked with the aid of sensor elements such as optical or electrical sensors.

In the tomograph 2 provided here in the exemplary embodiment, a patient couch 3 is present on which a patient 4 is located for recording measured data.

Furthermore, the imaging medical device 1 has a computing device 5 having an assigned display screen 6 with an input apparatus in the form of a keyboard. The tomograph 2 is used to record simultaneously temporally highly resolved magnetic resonance data and nuclear medicine PET measured data. From the temporally highly resolved magnetic resonance data, the computing device 5 connected to the tomograph 2 via a data connection determines movement information that it ultimately uses for the purpose of suitably adapting an attenuation correction map for the PET data.

In this example embodiment, this adaptation is carried out here such that static and movable components of the imaging medical device 1 are separated from one another in an initially present attenuation correction map. The static components in this case relate to such components as are to be ascribed to the absorption by fixed (immovable) device elements. In the example shown, these are the patient couch 3 already brought into position for the recording, and a fixed local coil 8 (illustrated here only diagrammatically). Depending on recording region, a movable component is, by contrast, to be ascribed, for example, to the patient fixing 7, which: moves with the patient 4.

The movable components of the attenuation correction map are now corrected with the aid of the movement information recorded simultaneously with the nuclear medicine data, an improvement in the image quality of the nuclear medicine image data being achieved, particularly in the case where strong movement operations are present. This movement correction of the attenuation correction map can be carried out repeatedly in the course of the measurement in the presence of new movement information.

Finally, FIG. 3 shows a schematic sketch of an embodiment of an inventive adaptation of an attenuation correction map 9. The attenuation correction map 9, which is merely sketched here, shows, as indicated by the different hatchings 10a-10f here, the spatial distribution of the absorption behavior in the measured data recording range.

During the conduct of an embodiment of the inventive method, the attenuation correction map 9 is now divided into static components 11 and movable components 12 of the appropriately separated attenuation correction map 13. To provide clarity, the static components 11 are illustrated in a fashion separated from the movable components 12 by lines 14. For the movable components 12, use is subsequently made of the movement information from the method of high temporal resolution in order to obtain an adapted attenuation correction map 15 that is adapted as regards the movable components to the current state of movement, that is to say here shows different correction information in accordance with the hatchings 16a-16d by comparison with the original hatchings 10a, 10c, 10e and 10f of the movable components. The unchanged static component is no longer shown here, for reasons of clarity.

Consequently, the nuclear medicine image quality can be improved, particularly in the case where a strong movement is present, by using an attenuation correction map conforming to the current state, that is to say the attenuation correction map 15, which is, if appropriate, adapted repeatedly during the data recording.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways. Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for recording measured data of a patient while taking account of movement operations by a medical device designed both for recording movement-related measured data with the aid of at least one of an imaging method and at least one sensor element, and also for recording nuclear medicine measured data, the method comprising:
   recording nuclear medicine measured data with the aid of the medical device;
   simultaneously recording movement-related measured data with the aid of the medical device;
   determining at least one item of movement information relating to at least one movement operation, at least one of of the patient and in the body of the patient, by evaluating by at least a portion of the recorded measured data of high temporal resolution on the part of a computing device of the medical device; and
   adapting at least one item of attenuation correction information available for the computing device and serving for reconstructing the nuclear medicine measured data, doing so as a function of the at least one determined item of movement information, wherein
      the at least one item of attenuation correction information available to the computing device is classified as static or moving items of attenuation correction information.

2. The method as claimed in claim 1, wherein at least one item of attenuation correction information forming a constituent of an attenuation correction map for a measured data recording range is adapted.

3. The method as claimed in claim 1, wherein at least one initial item of attenuation correction information, in particular an initial attenuation correction map, is determined for later adaptation from already recorded pictures of movement-related measured data.

4. The method, as claimed in claim 3, wherein the at least one item of attenuation correction information is adapted for a movement correction of the nuclear medicine measured data by using at least one imaging rule determined from the at least one item of movement information.

5. The method as claimed in claim 1, wherein a subsequent adaptation is carried out by taking exclusive account of the items of attenuation correction information classified as moving.

6. The method as claimed in claim 1, wherein at least one of
   at least one item of attenuation correction information relating to absorption by at least one of a patient table, at least one cladding part and a stationary local coil of the medical device is classified as static attenuation correction information, and
   at least one item of attenuation correction information relating at least one of to the patient, to a flexible local coil for a magnetic resonance data recording and to a patient fixing is classified as a moving item of attenuation correction information.

7. The method as claimed in claim 1, wherein the at least one item of movement information relating to a relative movement of the patient in relation to a static component of the medical device is determined from the recorded measured data and is used to adapt the at least one item of attenuation correction information.

8. The method as claimed in claim 1, wherein at least one of at least one of
   at least one of magnetic resonance data, computed tomography data, ultrasound data and sensor data is recorded as at least one of movement-related measured data, and
   at least one of positron emission tomography data and single photon emission computed tomography data is recorded as temporally less well resolved nuclear medicine measured data.

9. The method as claimed in claim 1, wherein, in parallel with the measured data, recording a movement correction is performed in real time by the computing device for at least a portion of the nuclear medicine measured data as a function of the at least one determined item of movement information.

10. A medical device, designed for recording movement-related measured data of a patient while simultaneously taking account of movement operations, with the aid of at least one of an imaging method and by way of at least one sensor element, and for recording nuclear medicine measured data, the medical device comprising:
    a computing device to determine at least one item of movement information relating to at least one movement operation, at least one of of the patient and in the body of the patient, by evaluating at least a portion of the recorded movement-related measured data, and designed to adapt at least one item of attenuation correction information available to the computing device and serve for reconstructing the nuclear medicine measured data as a function of the at least one item of determined movement information, wherein
       the at least one item of attenuation correction information available to the computing device is classified as static or moving items of attenuation correction information.

11. The method as claimed in claim 2, wherein at least one initial item of attenuation correction information is determined for later adaptation from already recorded pictures of movement-related measured data.

12. The method as claimed in claim 3, wherein the at least one initial item of attenuation correction information includes an initial attenuation correction map.

13. The method as claimed in claim 11, wherein the at least one initial item of attenuation correction information includes an initial attenuation correction map.

14. The method as claimed in claim 12, wherein the at least one item of attenuation correction information is adapted for a movement correction of the nuclear medicine measured data by using at least one imaging rule determined from the at least one item of movement information.

15. The method as claimed in claim 13, wherein the at least one item of attenuation correction information is adapted for a movement correction of the nuclear medicine measured data by using at least one imaging rule determined from the at least one item of movement information.

16. The method as claimed in claim 1, wherein all items of attenuation correction information of an attenuation correction map are classified accordingly for a measured data recording range.

17. A medical device, designed for recording movement-related measured data of a patient while simultaneously taking account of movement operations, with the aid of at least one of an imaging method and by way of at least one sensor element, and for recording nuclear medicine measured data, the medical device comprising:

means for recording nuclear medicine measured data with the aid of the medical device;

means for simultaneously recording movement-related measured data with the aid of the medical device;

means for determining at least one item of movement information relating to at least one movement operation, at least one of of the patient and in the body of the patient, by evaluating by at least a portion of the recorded measured data of high temporal resolution on the part of a computing device of the medical device; and means for adapting at least one item of attenuation correction information available for the computing device and serving for reconstructing the nuclear medicine measured data, doing so as a function of the at least one determined item of movement information, wherein the at least one item of attenuation correction information available to the computing device is classified as static or moving items of attenuation correction information.

18. A tangible computer readable medium including program segments for, when executed on a computer device, causing the computer device to implement the method of claim 1.

* * * * *